United States Patent
Burbank et al.

(10) Patent No.: US 7,229,465 B2
(45) Date of Patent: Jun. 12, 2007

(54) METHOD AND APPARATUS FOR THE DETECTION AND LIGATION OF UTERINE ARTERIES

(75) Inventors: Fred H. Burbank, Laguna Niguel, CA (US); Michael L. Jones, San Clemente, CA (US); R. J. Serra, Irvine, CA (US); Greig Altieri, Laguna Beach, CA (US); Jill Uyeno, Mission Viejo, CA (US); Yu-Tung Wong, Huntington Beach, CA (US); Randy Werneth, Poway, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 61 days.

(21) Appl. No.: 10/113,096

(22) Filed: Mar. 28, 2002

(65) Prior Publication Data

US 2002/0183771 A1    Dec. 5, 2002

Related U.S. Application Data

(60) Provisional application No. 60/279,477, filed on Mar. 28, 2001.

(51) Int. Cl.
*A61B 17/00* (2006.01)
*A61B 17/42* (2006.01)
*A61B 17/08* (2006.01)
*A61B 5/02* (2006.01)

(52) U.S. Cl. .............. 606/205; 606/119; 606/158; 600/504

(58) Field of Classification Search ............... 606/119, 606/157, 158, 205–207; 600/454–456, 462, 600/492, 504, 473; 128/898; 604/533
See application file for complete search history.

(56) References Cited

U.S. PATENT DOCUMENTS 2,400,251 A    5/1946    Nagel (Continued)

FOREIGN PATENT DOCUMENTS

DE    195 28 440 A    2/1997

(Continued)

OTHER PUBLICATIONS

Bateman, William M.D., "Treatment of intractable menorrhagia by bilateral uterine vessel, Interruption", *Am. J. Obst. & Gynec.* 89(6):825-827 (Jul. 15, 1964).

(Continued)

*Primary Examiner*—Julian W. Woo

(57) ABSTRACT

The invention provides devices, systems and methods for occluding arteries without puncturing skin or vessel walls. The devices, systems and methods for occluding arteries are configured to be applied to arteries externally of the arteries. Occlusion may be temporary or permanent, and may be partial or complete. Clamping a device to tissue near to an artery is effective to compress tissue around the artery and to indirectly compress the artery. The methods, devices and systems of the invention find use in, for example, treatment of uterine disorders and conditions which may be treated by occlusion of the uterine arteries. A uterine artery may be accessed via a patient's vagina by compressing a portion of the vaginal wall around a portion of a uterine artery to occlude a uterine artery. Clamping of an artery may also be performed by clamping a device directly onto an artery.

26 Claims, 3 Drawing Sheets

U.S. PATENT DOCUMENTS

| | | |
|---|---|---|
| 3,411,505 A | 11/1968 | Nobis |
| 3,777,740 A | 12/1973 | Hokanson |
| 3,779,248 A | 12/1973 | Karman |
| 4,120,302 A | 10/1978 | Ziegler |
| 4,226,240 A | 10/1980 | Walker, Jr. |
| 4,292,960 A | 10/1981 | Paglione |
| 4,428,374 A | 1/1984 | Auburn |
| 4,428,379 A | 1/1984 | Robbins et al. |
| 4,454,767 A * | 6/1984 | Shinkai et al. ............ 73/861.18 |
| 4,509,528 A | 4/1985 | Sahota |
| 4,589,419 A | 5/1986 | Laughlin et al. |
| 4,650,466 A | 3/1987 | Luther ........................ 604/95 |
| 4,757,823 A | 7/1988 | Hofmeister et al. |
| 4,770,175 A * | 9/1988 | McEwen ..................... 600/492 |
| 4,771,788 A | 9/1988 | Millar |
| 4,945,896 A | 8/1990 | Gade |
| 4,994,069 A | 2/1991 | Ritchart et al. |
| 5,037,430 A | 8/1991 | Hasson |
| 5,081,997 A | 1/1992 | Bosley, Jr. et al. |
| 5,108,408 A | 4/1992 | Lally |
| 5,197,972 A * | 3/1993 | Hakki ........................ 600/504 |
| 5,201,314 A | 4/1993 | Bosley et al. |
| 5,226,911 A | 7/1993 | Chee et al. |
| 5,275,166 A | 1/1994 | Vaitekunas et al. |
| 5,277,181 A | 1/1994 | Mendelson et al. |
| 5,289,821 A * | 3/1994 | Swartz ........................ 600/455 |
| 5,289,831 A | 3/1994 | Bosley |
| 5,336,231 A | 8/1994 | Adair |
| 5,368,034 A | 11/1994 | Isner |
| 5,383,922 A | 1/1995 | Zipes et al. |
| 5,427,108 A | 6/1995 | Bollinger |
| 5,456,693 A | 10/1995 | Conston et al. ............ 606/192 |
| 5,458,596 A | 10/1995 | Lax et al. |
| 5,488,958 A | 2/1996 | Topel et al. |
| 5,507,744 A | 4/1996 | Tay et al. ..................... 606/50 |
| 5,542,944 A | 8/1996 | Bhatta |
| 5,549,624 A | 8/1996 | Mirigian et al. |
| 5,549,824 A | 8/1996 | Trumpf et al. |
| 5,556,396 A | 9/1996 | Cohen et al. |
| 5,562,680 A | 10/1996 | Hasson |
| 5,582,617 A | 12/1996 | Klieman et al. |
| 5,588,960 A | 12/1996 | Edwards et al. |
| 5,598,841 A | 2/1997 | Taniji et al. |
| 5,614,204 A | 3/1997 | Cochrum .................... 424/423 |
| 5,662,680 A | 9/1997 | Desai |
| 5,672,153 A | 9/1997 | Lax et al. |
| 5,674,243 A | 10/1997 | Hale |
| 5,691,314 A | 11/1997 | Hodgen |
| 5,697,937 A | 12/1997 | Toma |
| 5,697,942 A | 12/1997 | Palti |
| 5,713,371 A | 2/1998 | Sherman et al. |
| 5,713,896 A | 2/1998 | Nardella |
| 5,713,942 A | 2/1998 | Stern et al. |
| 5,715,832 A | 2/1998 | Koblish et al. |
| 5,716,389 A | 2/1998 | Walinsky et al. |
| 5,720,743 A | 2/1998 | Bischof et al. |
| 5,747,637 A | 5/1998 | Shinoda et al. |
| 5,759,154 A | 6/1998 | Hoyns |
| 5,766,135 A | 6/1998 | Terwilliger |
| 5,769,791 A * | 6/1998 | Benaron et al. ............ 600/473 |
| 5,776,129 A | 7/1998 | Mersch |
| 5,792,059 A | 8/1998 | Furia et al. |
| 5,797,397 A | 8/1998 | Rosenberg |
| 5,800,378 A | 9/1998 | Edwards et al. |
| 5,817,022 A | 10/1998 | Vesely |
| 5,836,906 A | 11/1998 | Edwards |
| 5,840,033 A | 11/1998 | Takeuchi |
| 5,895,386 A | 4/1999 | Odell et al. |
| 5,899,861 A | 5/1999 | Friemel et al. |
| 5,910,484 A | 6/1999 | Haupert, Jr. ................. 514/25 |
| 5,911,691 A | 6/1999 | Mochizuki et al. |
| 5,916,173 A | 6/1999 | Kirsner |
| 5,921,933 A | 7/1999 | Sarkis et al. |
| 5,922,008 A | 7/1999 | Gimpelson |
| 5,941,889 A | 8/1999 | Cermak |
| 5,979,453 A | 11/1999 | Savage et al. ............ 128/898 |
| 6,013,088 A | 1/2000 | Karavidas |
| 6,015,541 A | 1/2000 | Greff et al. |
| 6,019,724 A | 2/2000 | Gronningsaeter et al. |
| 6,032,673 A | 3/2000 | Savage et al. ............ 128/898 |
| 6,033,398 A | 3/2000 | Farley et al. |
| 6,034,477 A | 3/2000 | Peeters et al. |
| 6,035,238 A | 3/2000 | Ingle et al. |
| 6,045,508 A | 4/2000 | Hossack et al. |
| 6,066,139 A | 5/2000 | Ryan et al. |
| 6,077,257 A | 6/2000 | Edwards et al. |
| 6,080,118 A | 6/2000 | Blythe |
| 6,106,473 A | 8/2000 | Violante et al. |
| 6,152,874 A | 11/2000 | Looney et al. |
| 6,169,914 B1 | 1/2001 | Hovland et al. |
| 6,175,751 B1 | 1/2001 | Maizes |
| 6,210,330 B1 | 4/2001 | Tepper |
| 6,231,515 B1 | 5/2001 | Moore et al. |
| 6,254,601 B1 | 7/2001 | Burbank et al. |
| 6,261,234 B1 | 7/2001 | Lin |
| 6,280,441 B1 | 8/2001 | Ryan |
| 6,293,954 B1 | 9/2001 | Fogarty |
| 6,368,340 B2 | 4/2002 | Malecki et al. |
| 6,371,973 B1 | 4/2002 | Tepper |
| 6,602,251 B2 | 8/2003 | Burbank et al. |
| 6,610,074 B2 | 8/2003 | Santilli |
| 6,635,017 B1 | 10/2003 | Moehring et al. |
| 6,709,430 B2 * | 3/2004 | Doten et al. ................. 604/533 |
| 6,905,506 B2 | 6/2005 | Burbank et al. |
| 2002/0111537 A1 | 8/2002 | Taylor et al. |
| 2002/0165579 A1 | 11/2002 | Burbank et al. |
| 2002/0188306 A1 | 12/2002 | Burbank et al. |
| 2003/0120306 A1 | 6/2003 | Burbank et al. |

FOREIGN PATENT DOCUMENTS

| | | |
|---|---|---|
| EP | 0 472 368 | 2/1992 |
| EP | 0 598 579 | 5/1994 |
| EP | 0 890 342 A | 1/1999 |
| EP | 1 072 282 | 1/2001 |
| FR | 1 220 773 A | 5/1960 |
| GB | 2054026 | 6/1979 |
| GB | 2 302 025 A | 1/1997 |
| GB | 2 311 468 A | 1/1997 |
| WO | WO 95/02370 | 1/1995 |
| WO | WO 95/02371 | 1/1995 |
| WO | WO 98/19713 | 5/1998 |
| WO | WO 99/11179 A | 3/1999 |
| WO | WO 01/68720 | 9/2001 |
| WO | WO 01/80713 | 11/2001 |
| WO | WO 02/00192 | 1/2002 |
| WO | WO 02/078521 | 10/2002 |

OTHER PUBLICATIONS

Brigato, G. et al., "A Noninvasive Instrumental Method in Severe Postpartum Hemorrhages", *Minerva Ginecologica* 50(7-8):337-339 (1998).

Ravina, J. H. et al., "Arterial embolisation to treat uterine myomata", *The Lancet* 346:671-672 (Sep. 9, 1995).

Garza Leal, J. et al., "Myoma Treatment by Transient Uterine Ischemia" *The Journal of the American Assoication of Gynecologic Laparoscopists* 7(3):S31 (Aug. 2000).

Fuchs, Karl, "Afibrinogenemia Treated by Ligation of Uterine Arteries" *Gynacologic* 148:407-411 (1959).

O'Leary, James A, M.D. "Uterine Artery Ligation in the Control of Postcesarean Hemorrhage" *Am. J. Obst. & Gynec.* 94(7):920-924 (Apr. 1, 1996).

O'Leary, James L., M.D. et al., "Uterine artery ligation in the control of intractable postpartum hemorrhage" *Am. J. Obst. & Gynec.* 94(7):920-924 (Apr. 1, 1966).

Barth, K.H. et al, Long Term Follow-up or Transcatheter Embolization with Autologous Clot, Oxygel and Gelform in Domestic Swine, *Investigative Radiology*, May-Jun. 1977, vol. 12, No. 2, pp. 277-278.

Brohim, R.M. et al., "Development of Independent Vessel Security After Ligation With Absorbable Sutures or Clips", *The American Journal of Surgery*, Mar. 1993, vol. 165, pp. 345-349.

Burbank, Fred et al., "Uterine Artery Occlusion by Embolization or Surgery for the Treatment of Fibroids: A Unifying Hypothesis—Transient Uterine Ischemia", *The Journal of the American Association of Gynecologic Laparoscopists*, Nov. 2000, vol. 7, No. 7 Supplemental, pp. S3-S49.

Hay, D.L. et al., "Hemostasis in Blood Vessels After Ligation", *Am. J. Obstet. Gynecol.*, Mar. 1989, 160:3, pp. 737-739.

Hunerbein, M. et al., "Endoscopic Ultrasound-Guided Real Time Biopsy of Peri-Intestinal Tumors", *Surgical Technology International VII*, 1998, pp. 91-95.

O'Leary, James A., M.D., "Uterine Artery Ligation in the Control of Postcesarean Hemorrhage", *The Journal of Reproductive Medicine, Inc.*, 40(3):189-193 (Mar. 1995).

Schaefer, C.J. et al., "Absorbable Ligating Clips", *Surg. Gynecol. Obstet.*, 1982, 154:513-516.

"Mick 200-TP Applicator Package", Mick Radio-Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostrate Gland", Bruel & Kjaer Medical Systems, Inc., advertisement.

International Search Report for PCT/US2004/038276, mailed Mar. 15, 2005.

International Search Report for PCT/US2004/038111, mailed May 3, 2005.

Written Opinion for PCT/US2004/038111, mailed May 3, 2005.

Translation for FR 1 220 773.

International Preliminary Report of Patentability for Serial No. PCT/US04/01935, mailed Jul. 8, 2005.

International Search Report for PCT/US02/09775, mailed Sep. 12, 2002.

International Search Report for PCT/US02/09549, mailed Jun. 30, 2003.

International Search Report for PCT/US03/35815 mailed Jun. 30, 2004.

* cited by examiner

METHOD AND APPARATUS FOR THE DETECTION AND LIGATION OF UTERINE ARTERIES

CROSS-REFERENCE TO RELATED APPLICATIONS

This application is related to U.S. Provisional Application No. 60/279,477 filed Mar. 28, 2001, hereby incorporated by reference in its entirety and from which benefit is hereby claimed under 35 U.S.C. 119(e).

FIELD OF THE INVENTION

The invention relates generally to the field of treatment of diseases and conditions by regulation of blood flow; in particular, the treatment of a uterus by regulating blood flow thereto.

BACKGROUND OF THE INVENTION

Hysterectomy (surgical removal of the uterus) is performed on approximately 600,000 women annually in the United States. For approximately 340,000 women, hysterectomy is probably the best current therapeutic choice for the treatment of their diseases (uterine cancer, endometriosis, menorrhagia, and prolapse). For approximately 60,000 women with dysfunctional uterine bleeding (abnormal menstrual bleeding that has no discrete anatomic explanation such as a tumor or growth), newer endometrial ablation techniques may be an alternative to hysterectomy. For approximately 200,000 women with benign but symptomatic (excessive bleeding, pain, and "bulk" sensations) muscular tumors of the uterus, known as leiomyoma or fibroids, newer treatment methods have been developed which may spare these women a hysterectomy, as well.

Hysterectomy for treating uterine fibroid disorders, though effective, has many undesirable characteristics. Thus, any method which can approximate the therapeutic result of a hysterectomy without removing the uterus (and commonly the ovaries since they are closely adjacent to the uterus) would be a significant improvement in this field.

The undesirable characteristics of hysterectomy include a known mortality rate of 0.5 deaths per 1000 hysterectomies. Stated another way, the risk of death within 30 days of hysterectomy is thirty times greater for women who have had a hysterectomy than for women of similar ages and backgrounds who have not had a hysterectomy. Morbidity (medical symptoms and problems short of death) associated with hysterectomy include possible injury to adjacent organs (the bladder, the ureters, and bowel), hospital stay of approximately one week, five to six weeks of slow recovery to normal activity, three weeks of absence from work, direct medical expenses of at least $10,000, indirect cost of time away from work, a future three-fold increase in the incidence of cardiovascular disease, decreased sexual pleasure in approximately thirty percent of women, and depression and anxiety for many years after the hysterectomy for approximately eight percent of women.

The endometrium is a glandular mucous membrane of the uterus, the thickness and structure of which varies with the phase of the menstrual lining. It is normal for portions of the lining to slough off and bleed during menstruation, but many women suffer from painful dysfunctional uterine bleeding or endometritis. Thus, endometrial ablation (removal or destruction of the endometrium) may be an alternative to hysterectomy for approximately 60,000 women. A great many new devices have been invented to perform endometrial ablation to treat dysfunctional uterine bleeding. To distinguish the present invention and its applications from endometrial ablation devices, the endometrial ablation devices will be briefly described. Endometrial devices can be categorized into two major groups: devices which require direct visualization of the endometrium to apply an energy source to ablate the endometrium; and those that do not require visualization for their application.

Direct visualization of the lining of the uterus is accomplished by placing a hysteroscope through the vagina and into the uterus via the cervical os (opening). The hysteroscope image is then displayed as a color image on a TV monitor adjacent to the patient. The gynecologist then manipulates the hysteroscope and endometrial ablation instrument to ablate the lining of the uterus. Endometrial lining ablation instruments directed by hysteroscope include radio frequency or electrosurgery loops, roller-balls, and lasers. The goal of all of these hysteroscopic endometrial ablation instruments is to transfer heat energy to the endometrium sufficiently to heat and thereby destroy it. An ablated endometrium cannot respond physiologically or pathologically to hormonal stimulation and cannot, therefore, proliferate and bleed.

To treat all of the endometrium, it must be entirely visible through the hysteroscope. However, visualization of all of the endometrium is difficult. The uterus must be distended like a water balloon to allow adequate visualization. In this distension process, some women become water intoxicated and hyponatremic. Furthermore, the uterine cavity is an awkward shape, somewhat triangular and often angulated. Directly visualizing each and every square millimeter of endometrial surface and ablating each and every square millimeter is seldom achieved. Consequently, portions of the dysfunctional endometrium may persist and dysfunctional bleeding may continue.

Because of these hysteroscopic visualization and ablation limitations, alternative methods have been invented to destroy the lining of the uterus without the need at all for visualization of the uterine lining. On such method uses a prototypic instrument, the ThermaChoice™ balloon, which is produced by GyneCare, a division of Ethicon, Inc. (see U.S. Pat. No. 5,776,129, incorporated in its entirety herein). This device is inserted through the vagina into the uterus via the cervical os. The balloon is shaped like a triangle to conform to the shape of the uterus. Once in place, hot fluid is added to the balloon to heat and destroy the uterine lining. Treatment only occurs where the balloon is in adequate contact with the uterine lining. As an alternative, hot fluids can be directly introduced into the uterus (e.g., ENABL brand system manufactured by Innerdyne, Inc., and marketed by U.S. Surgical Corporation).

Endometrial destruction can also be brought about with chemical damage, photochemical injury, or thermal damage (heat or cold). Energy that reaches and destroys the cells of the endometrial lining of the uterus potentially destroys the uterine lining and thereby treats dysfunctional uterine bleeding.

Surgically removing fibroids or in situ ablation of uterine fibroids is a bit like eradicating ants in the pantry—they are not all seen from one perspective and there may be a lot of them. Commonly, a diagnosis of uterine fibroids involves the presence of multiple fibroids, often averaging ten fibroids or more per afflicted uterus. Consequently, it is difficult to know which fibroid is causing symptoms to the patient (bleeding, pain, and bulk effects on adjacent organs). Furthermore, fibroids occur at different layers in the uterus.

Uterine fibroids can occur adjacent to the lining of the uterus (submucosal fibroid), in the myometrium (intramural fibroid), or adjacent to the outer layer of the uterus (subserosal fibroid). Consequently, if one is directly observing the uterus from the peritoneal cavity, only subserosal fibroids would be seen. If one is directly observing the uterus from the endometrial surface of the uterus, only the submucosal would be seen. Fibroids deep within the wall of the uterus are poorly visualized from either surface. Finally, since fibroids come in all sizes, only the larger fibroids will be seen in any case.

Clearly, the strategy of identifying which individual fibroid is causing symptoms (when there are often many), finding that fibroid, and then either removing or destroying that individual fibroid is a rather complex strategy. It is therefore easy to understand why the hysterectomy is such a common surgical choice. With hysterectomy, all uterine fibroids are removed in one stroke.

In 1995, it was demonstrated that fibroids, in a uterus that contained one or multiple fibroids, could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 346; pp. 671–672, incorporated in its entirety herein). This technique is known as "uterine artery embolization". The technique uses standard interventional radiology angiographic techniques and equipment, whereby the uterine arteries are accessed via a transvascular route from a common femoral artery into the left and right uterine arteries.

Three facts explain the success of uterine artery embolization. First, it has been established that pelvic bleeding from a wide variety of sources (e.g., auto accidents, surgical errors, and post partum hemorrhage) can be effectively controlled with embolization techniques using coils placed in arterial and venous lumens (U.S. Pat. Nos. 4,994,069, 5,226,911, and 5,549,824, all of which are incorporated in their entireties herein) (available from Target Therapeutics), or particles (GELFOAM pledgets, available from Upjohn, Kalamazoo, Mich., or IVALON particles, available from Boston Scientific).

Second, fibroids live a tenuous vascular life with very little ability to recruit a new blood supply from the host when the primary blood supply is compromised. Third, the uterus has a dual (or redundant) blood supply, the primary blood supply being from the bilateral uterine arteries, and the secondary blood supply from the bilateral ovarian arteries.

Consequently, when both uterine arteries are occluded, i.e. bilateral vessel occlusion, the uterus and the fibroids contained within the uterus are both deprived of their blood supply. However, as demonstrated by Ravina et al., the effect on the fibroid is greater than the effect on the uterus. In most instances, the fibroid withers and ceases to cause clinical symptoms.

The uterine artery embolization technique utilized by Ravina et al. uses standard transvascular equipment, available in typical interventional radiology angiography suite. This equipment includes guide catheters to selectively enter the tortuous right and left uterine arteries, Ivalon or Gelfoam particles, and intravascular coils. With skill and these standard angiographic tools, the uterine arteries can be occluded bilaterally and fibroid disease treated through a 2 mm hole in the right groin and through the right common femoral artery. Following the procedure, the arterial puncture site is held with manual pressure for fifteen minutes. While post-procedural pain is often significant, and requires intravenously delivered pain medication, the patient is typically fully recovered in a few days.

One problem with present methods of uterine artery embolization is that many physicians do not possess the skill or equipment necessary to perform catheter-based uterine artery embolization under radiologic direction. Accordingly, only hundreds of uterine artery embolizations have been performed, worldwide, over the past three years, whereas hundreds of thousands of hysterectomies have been performed each year for uterine fibroids which are symptomatic.

What is needed, therefore, are devices and methods to occlude arteries such as the uterine arteries.

SUMMARY OF THE INVENTION

The invention is directed to devices, systems and methods for occluding arteries such as the uterine arteries. In particular, the invention is directed to devices, systems and methods for occluding arteries from outside the arteries; that is, to devices, systems and methods configured to be applied to arteries externally of the arteries. Occlusion may be temporary or permanent, and may be partial or complete. One method of occluding an artery comprises clamping the artery so that blood flow through the artery is reduced, or is completely stopped. Such clamping of an artery may be direct or may be indirect. Thus, clamping of an artery may be accomplished by applying a clamping device directly onto an artery effective to compress the artery, or may be accomplished by applying a clamping device to tissue near to an artery effective to compress the artery.

Clamping devices embodying features of the invention include clamping devices having a clamping member configured to apply pressure to a blood vessel and a blood flow sensor. A clamping member may have a distal portion configured to engage tissue. Clamping devices embodying features of the invention may have two, or more, clamping members. Two clamping members maybe disposed opposite each other and configured to move or apply pressure towards each other, such as to close together, effective to engage tissue and to clamp a blood vessel between them. Alternatively, a clamping member may have two portions disposed in apposition to one another, effective to clamp tissue between the portions.

A blood flow sensor preferably includes doppler ultrasound sensor. A blood flow sensor may be disposed on a clamping member, preferably on a distal portion configured to engage tissue, more preferably near the middle of the distal portion. A blood flow sensor disposed on a clamping member may be configured to detect blood flow in a blood vessel near said clamping member, and may be configured to detect blood flow in a blood vessel clamped by a clamping member. Clamping devices embodying features of the invention may include more than one blood flow sensor.

Clamping devices may be configured to be held by a clamping device applicator. A clamping device applicator embodying features of the invention may be used to deliver a clamping device to a desired location. A clamping device applicator includes an engagement member configured to hold and to release a clamping device, and a delivery member configured to deliver a clamping device to a desired location. A clamping device applicator may be used to close together clamping members of a clamping device, to apply pressure to clamping members, and to apply pressure to tissue disposed between clamping members of a clamping device. A clamping device applicator may include an elongated arm or arms effective to place a clamping device at a desired location within a patient's body, such as adjacent a vaginal wall within a vagina near to a uterine artery.

Clamping device embodying features of the invention may be configured to lock into a clamping position. Such a locked configuration may be temporary and releasable, or may be permanent. Clamping devices embodying features of the invention may have a ratchet mechanism configured to hold at least one clamping member in a clamping position; such ratchet mechanisms may be releasable ratchet mechanisms.

Clamping devices embodying features of the invention may include a release mechanism configured to release a locking mechanism such as a ratchet effective to release the clamping of a blood vessel. Clamping devices embodying features of the invention may include a recovery member configured to aid the removal of the clamping device from a patient and the recovery of the device after release of the clamping of a blood vessel. For example, a recovery member may include a lanyard or other cord or cable device.

The invention further provides systems for occluding a blood vessel, including a clamping device having a clamping member configured to apply pressure to a blood vessel, and a blood flow sensor, and a clamping device applicator configured to engage a clamping device. The blood flow sensor in such systems is preferably a doppler ultrasound sensor.

Methods and devices embodying features of the invention may be used to occlude any artery; in the following discussion, the uterine artery is used as an example. It will be understood that the methods and devices discussed in regard to this example may also be applied to any other artery.

One method of occluding a uterine artery includes applying a clamping device to the artery so that blood flow through the artery is reduced, or is completely stopped. Such clamping of a uterine artery may be direct or may be indirect. Clamping of the artery may be accomplished by applying a clamping device directly onto a uterine artery effective to compress the uterine artery, or may be accomplished by applying a clamping device to tissue near to a uterine artery effective to compress the uterine artery.

A method of occluding an artery includes sensing an artery, and compressing an artery with a clamping device having a blood flow sensor. Sensing an artery may include sensing blood flow, such as blood flow in an artery. Compressing an artery may include grasping tissue near to an artery, and may include compressing tissue surrounding an artery effective to compress the artery.

Thus, a method of occluding a uterine artery includes sensing a uterine artery, and compressing a uterine artery with a clamping device having a blood flow sensor. Accessing a uterine artery may include accessing a uterine artery via the vagina of a patient with a uterine artery. Compressing a uterine artery may include grasping tissue near to a uterine artery, and may include compressing tissue surrounding a uterine artery effective to compress the uterine artery. A method of occluding a uterine artery includes accessing a uterine artery via a vagina, and compressing a portion of a vagina wall with a clamping device having a blood flow sensor. A method of occluding uterine artery may also include sensing blood flow in a uterine artery. Sensing blood flow in a uterine artery may include sensing blood flow in a uterine artery through a wall of a vagina. A method of occluding blood flow in a uterine artery may include sensing a reduction or cessation of blood flow following application of a clamping device.

A method of occluding a uterine artery includes applying a clamping device having a blood flow sensor to the artery so that blood flow through the artery is reduced, or is completely stopped, and the reduction or cessation of blood flow is sensed by the blood flow sensor. A blood flow sensor is also effective to locate the artery by sensing blood flow before application of the clamping device. A particularly suitable blood flow sensor is a doppler ultrasound sensor. A uterine artery may be clamped effective to compress the uterine artery by applying a clamping device directly onto a uterine artery, or by applying a clamping device to tissue near to a uterine artery.

A method of occluding a uterine artery of a patient includes compressing a portion of a uterine artery with a clamping device comprising a blood flow sensor, and sensing a level of blood flow in the artery with said blood flow sensor. For example, the method may include sensing blood flow in a uterine artery effective to locate a uterine artery. A uterine artery may be accessed via the vagina of a patient, and compressing a uterine artery may be accomplished by compressing a portion of the vaginal wall around a portion of a uterine artery. A clamping device suitable for use in a method embodying features of the invention may be a releasable clamping device, so that a uterine artery may remain occluded for only a limited time. A suitable limited time may be between about 0.2 hours and about 12 hours, or preferably between about 0.5 hours and about 4 hours.

The devices, systems and methods of the present invention may be used to occlude blood flow in arteries without need for invasive procedures such as puncturing skin or vessel walls. For example, clamping a vaginal wall around a uterine artery is effective to occlude blood flow in that uterine artery without puncturing the skin or a blood vessel of the patient. Such occlusion may be used to treat uterine disorders such as, for example, uterine fibroids, dysfunctional uterine bleeding, and other uterine disorders.

The devices, systems and methods of the present invention provide the advantages of allowing for the occlusion of an artery without puncture of bodily tissue, and allowing for arterial occlusion without need for radiographic equipment or skill in the use of radiographic techniques. The devices and methods are simpler and more readily used and removed than other methods and devices, and provide improved treatments for serious conditions and diseases.

DETAILED DESCRIPTION OF THE PREFERRED EMBODIMENTS

Figure 1:
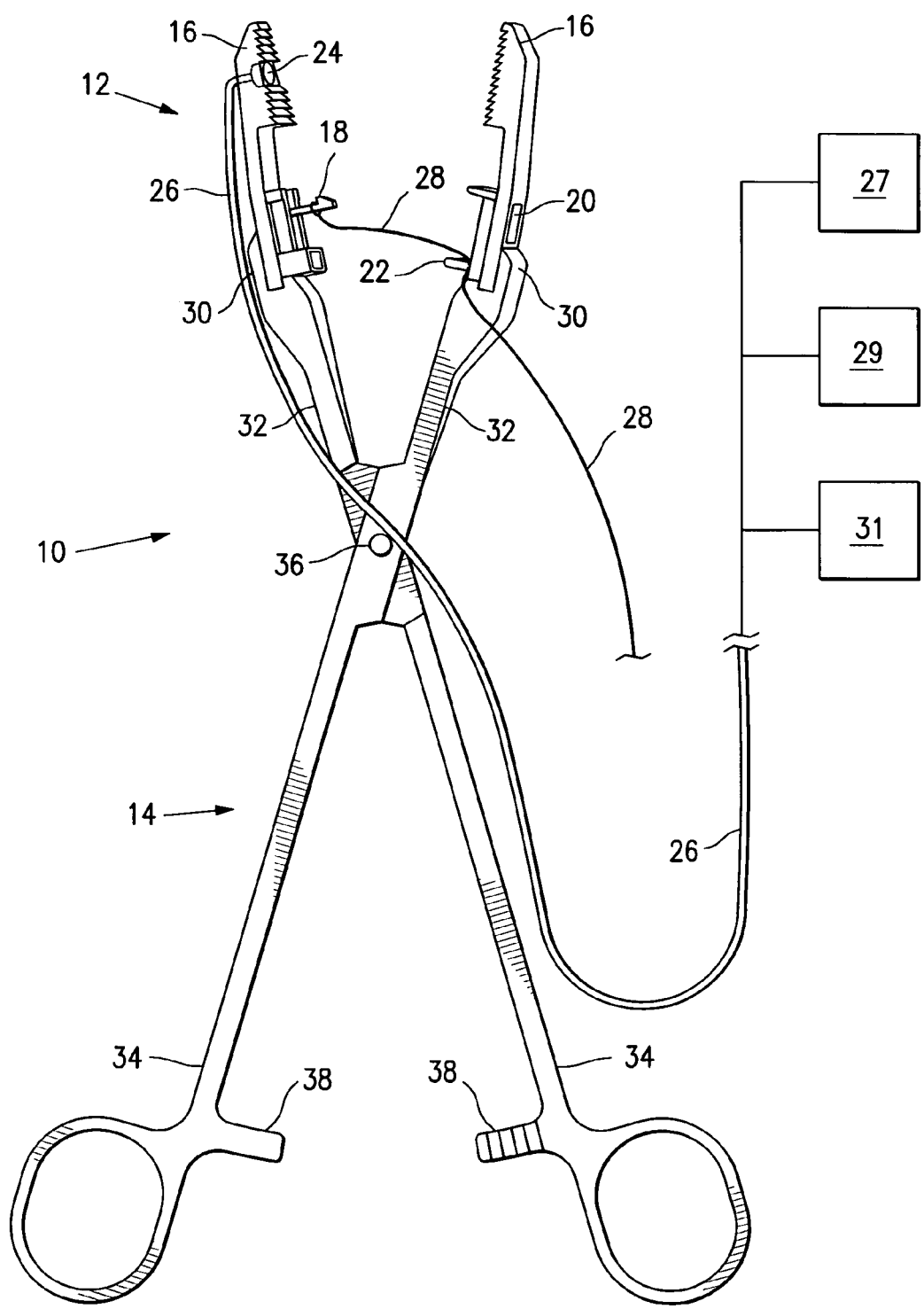
FIG. 1 is a perspective view of a system embodying features of the invention including a clamping device and a clamping device applicator embodying features of the invention.

FIG. 1 shows a system 10 embodying features of the invention including a clamping device 12 and a clamping device applicator 14 embodying features of the invention. The clamping device shown in FIG. 1 is a clamp 12 having clamp jaws 16 which act as clamping members. The clamp jaws 16 are shown separated, but may be locked together by action of the clamp device applicator 14 bringing together locking mechanism components detent 18 and catch 20 effective to lock jaws 16 together. Placement of jaws 16 against tissue, such as vaginal wall tissue, surrounding an artery, such as a uterine artery, is effective to compress an artery between jaws 16 and to clamp and lock together jaws 16 to maintain such compression for a desired length of time. Clamp 12 also has a mounting portion 22 configured to engage a clamp device applicator.

FIG. 1 further illustrates blood flow sensor 24 located on a jaw 16 where it may sense blood flow in an artery within tissue near a clamp 12. Blood flow sensor cable 26 is effective to carry electrical power and electrical signals to and from power apparatus 27, sensing apparatus 29 and control apparatus 31 all of which are operably connected to the blood flow sensor 24 via a cable 26. As is known in the art, such power, sensing and control apparatus are effective to operate a blood flow sensor 24 and to provide an operator with blood flow information sensed by a blood flow sensor 24. The power, control and sensing functions illustrated in FIG. 1 by separate power apparatus 27, sensing apparatus 29 and control apparatus 31 may alternatively be performed by two or by one apparatus combining some or all of these functions. Release and recovery of the clamp 12 may be effected by a lanyard 28, as illustrated in FIG. 1, or by other suitable means.

A clamp device applicator 14 is configured to hold a clamp 12 and to deliver it to a desired location, and optionally to apply force effective to compress tissue and optionally to lock a clamp 12 into a desired configuration. The clamp applicator 14 shown in FIG. 1 has clamp holders 30 configured to engage a clamp 12, mounted on arms 32 which are operably connected to handles 34, as by applicator pivot 36 shown in FIG. 1, to provide mechanical support for and to allow the application of force to a clamp 12. A clamp device applicator may be locked into a desired configuration with an applicator lock, such as the applicator lock 38 illustrated in FIG. 1.

Figure 2:
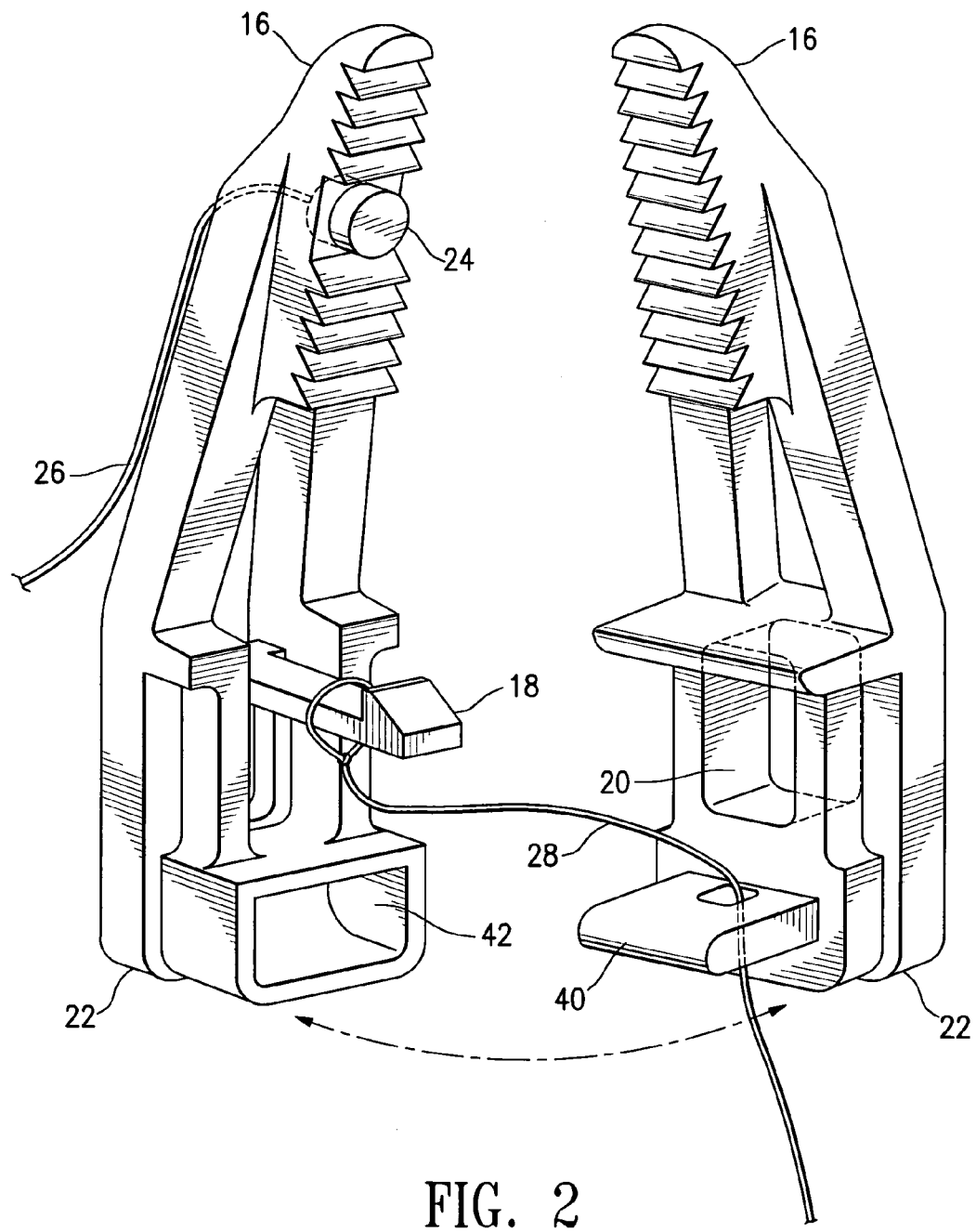
FIG. 2 is a perspective view of a two portions of a clamping device embodying features of the invention.

FIG. 2 is a perspective view of a two portions of a clamping device 12 embodying features of the invention, shown free of a clamp applicator 14. Jaws 16 are configured to engage and hold tissue, and may be locked together by a locking mechanism shown here comprising detent 18 and catch 20. Also shown are guide members 40 and 42 configured to guide the engagement of jaws 16 together. Extending guide member 40 is configured to fit within enclosing guide member 42 and to aid in the proper location and fitting of jaws 16 when jaws 16 approach one another in a compressing engagement effective to compress tissue, including vascular tissue, between jaws 16.

Figure 3:
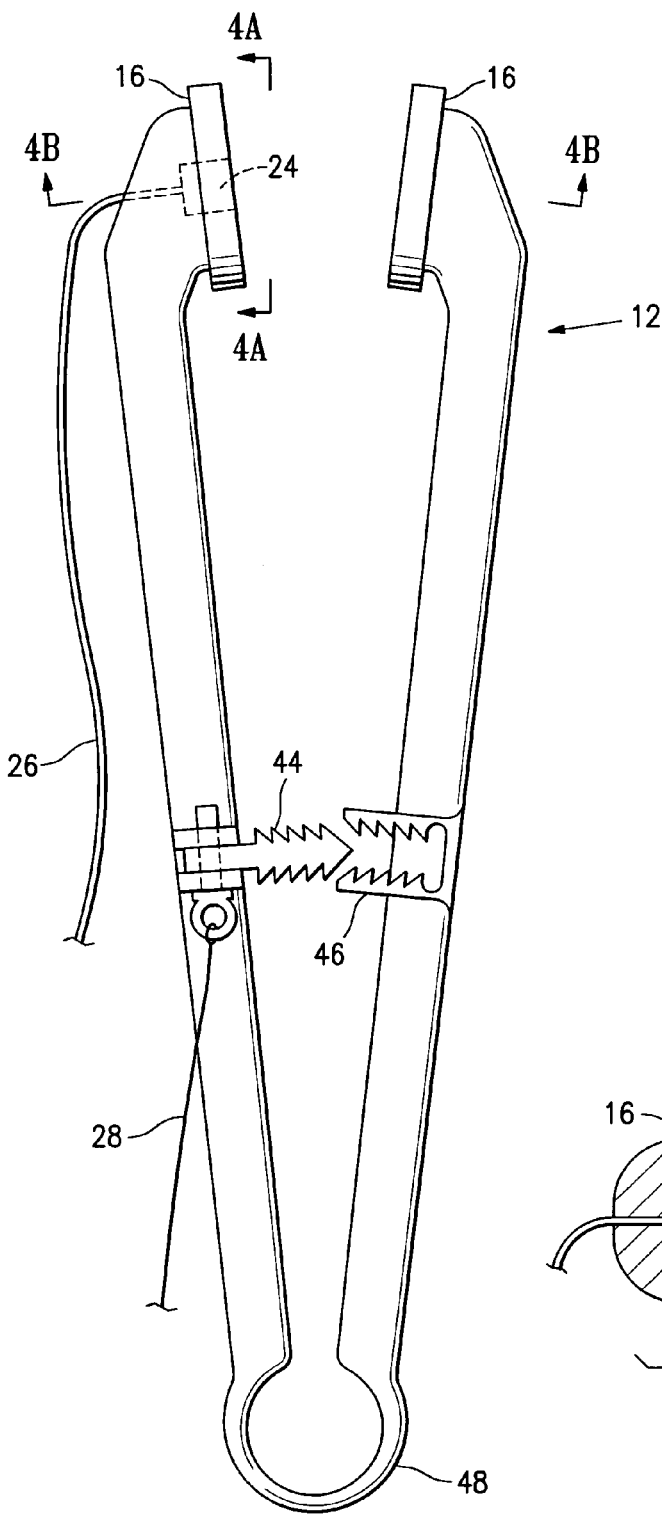
FIG. 3 is an elevational view of a clamping device embodying features of the invention.

FIG. 3 illustrates an alternative embodiment of a clamp 12 embodying features of the invention. This clamp 12 comprises a single clamp 12 with two jaws 16 connected by clamp pivot 48. A locking mechanism including a pawl 44 and a ratchet 46 are configured to engage with each other to lock jaws 16 in a desired configuration. Also shown are a blood flow sensor 24 with cable 26, and a lanyard 28.

Figure 4A:
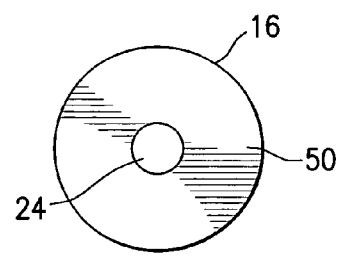
FIG. 4A is a plan view of a portion of a clamping member of the clamping device of FIG. 3 embodying features of the invention.

FIG. 4A is a plan view of a portion of a portion of a jaw 16 of the clamping device 12 illustrated in FIG. 3 embodying features of the invention. A clamping surface 50 is shown, with a blood flow sensor 24 disposed on the clamping surface 50.

Figure 4B:
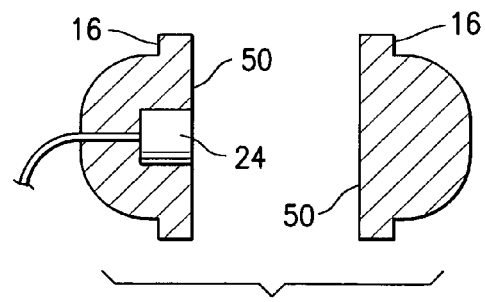
FIG. 4B is a transverse cross-sectional view of the clamping device of FIG. 3 taken at line 4B-4B.

FIG. 4B is a transverse cross-sectional view of the clamping device 12 of FIG. 3 taken at line 4B-4B showing portions of the jaws 16, clamping surface 50 and blood flow sensor 24 in.

Clamping devices embodying features of the invention include clamps, ratchets, jaws, clips, wires, sutures, coils, or other structures or devices. Clamping devices preferably include at least one clamping member configured to directly or indirectly apply pressure to a blood vessel or to urge movement of a blood vessel. Clamping devices may also include a clamping surface, such as an anvil, against which a blood vessel may be directly or indirectly urged. A clamping member may serve as a clamping surface for another clamping member. A clamping member may be configured to urge a blood vessel towards a clamping surface or towards another clamping member. Methods for applying clamping devices include grasping, probing, penetrating, deflecting, invaginating, and dilating tissue or vessels.

Clamping devices embodying features of the invention may also include at least one blood flow sensor configured to sense blood flow in vessels. A blood flow sensor is preferably disposed on a clamping member, such as a jaw of a clamp, in a position to sense blood flow near a clamping member when the clamping device is near to a blood vessel, and in a position to contact a blood vessel when the clamping device is applied directly to a blood vessel. Alternatively, a blood flow sensor may be disposed on a clamping surface, or other location on a clamping device effective to sense blood flow in vessels near the clamping device and to aid in guiding the clamping device to a desired location near a blood vessel. A particularly suitable blood flow sensor is a doppler ultrasound sensor.

Clamping devices may be of any suitable size, which is determined in part by the location and dimension of the artery to be occluded. For accessing and occluding a uterine artery, the dimensions of a vagina help to determine suitable sizes for clamping devices and clamp applicators embodying features of the invention. For example, a clamping device may be between about 2 cm and about 20 cm in length, preferably between about 3 cm and about 15 cm in length.

A clamping device may be applied alone, or may be applied with a clamping device applicator. A clamping device that is applied to a blood vessel using a clamping device applicator may be configured to be received by the applicator, and to be applied by it. A clamping device applied by an applicator may have a clamping member configured to move under the influence of a clamping device applicator. Where a clamping device has a plurality of clamping members, some clamping members may be configured to close or to close together under the influence of a clamping device applicator.

Clamping devices embodying features of the invention may be made from any suitable material or combination of materials, including metals such as stainless steel and shape memory alloys such as nickel titanium alloys, plastics, ceramics, and other biocompatible materials known in the art. Biocompatible polymers, such as for example, polycarbonate, polysulfone, polyester, polyacetal, and other polymers may be particularly suitable for embodiments of the invention.

Blood flow sensors may be any blood flow sensor. Preferred blood flow sensors include doppler or near infra-red blood flow sensors. A sensing box may be included to receive and process data in the analysis of blood flow. A clamping system may be configured to provide Doppler, near infra-red spectrometric imaging of arteries to non-destructively locate and ligate or occlude identified arteries. The device or system may be designed for single use (disposable) or may be sterilizable and capable of multiple use.

The invention claimed is:

1. An intravaginal clamping device for occluding a female patient's uterine artery, comprising:
   a) a pair of releasable clamping members which are configured to press against the patient's vaginal tissue, which have opposed clamping surfaces and which are releasably lockable in a clamped configuration to apply pressure to the patient's vaginal tissue to occlude an underlying uterine artery,
   b) an ultrasonic blood flow sensor on at least one of the clamping surfaces for locating the patient's uterine artery or for detecting blood flow therethrough, and
   c) a delivery mechanism comprising connected handles, wherein each of the clamping members is releasably secured to clamp applicators on distal portions of said handles.

2. The clamping device of claim 1, wherein said blood flow sensor comprises a doppler ultrasound sensor.

3. The clamping device of claim 1 wherein the pair of clamping members are disposed with clamping surfaces thereof in an opposing relationship with respect to each other.

4. The clamping device of claim 3, wherein the clamping members are configured to be closed together so that at least one clamping surface thereof applies sufficient pressure to the patients uterine artery to at least partially occlude the artery.

5. The clamping device of claim 3, wherein the two clamping members are configured to be closed together by said clamp applicators.

6. The clamping device of claim 1, wherein the clamping members are lockable by a ratchet mechanism configured to hold the clamping members in a clamping position.

7. The clamping device of claim 6, wherein said ratchet mechanism has an unlocking mechanism.

8. The device of claim 7 wherein the unlocking mechanism is a cord.

9. The device of claim 8 wherein the cord is a lanyard.

10. The clamping device of claim 1, wherein the clamping surfaces of the clamping members are on distal portions of the clamping members.

11. The clamping device of claim 10, wherein the blood flow sensor is disposed on a damping surface of at least one of the clamping members.

12. The device of claim 1 wherein the pair of releasable clamping members has an extending guide member configured to fit within an enclosing guide member.

13. The clamping device of claim 1 including a clamping device applicator configured for intravaginal delivery and having one elongated member configured to releasably engage one clamping member and one elongated member configured to releasably engage the other clamping member.

14. The device of claim 13, wherein said blood flow sensor comprises a doppler ultrasound sensor.

15. The device of claim 13, comprising a plurality of blood flow sensors.

16. The device of claim 13 wherein at least one of the clamping members has a recovery member.

17. The device of claim 16, wherein said recovery member comprises a lanyard.

18. The system of claim 13 wherein the releasable clamping assembly has an extending guide member configured to fit within an enclosing guide member.

19. The uterine artery occluding device of claim 18 wherein the blood flow sensor on the pressure applying surface of one of the releasable clamping elements has a sensing direction toward the pressure applying surface of the other releasable clamping element.

20. A method of treating a uterine disorder in a female patient by occluding a uterine artery of the patient, comprising:
   providing a clamping device which is releasably mounted to a clamping device applicator configured for intravaginal delivery, which has a pair of clamping members with clamping surfaces configured to apply pressure to the patient's uterine artery, which is lockable in a pressure applying configuration, and which has a blood flow sensor on a clamping surface;
   compressing a portion of the patients uterine artery by locking at least one clamping member of the clamping device against the patient's vaginal tissue adjacent to the uterine artery to compress the underlying uterine artery; and
   sensing a level of blood flow in the uterine artery with said blood flow sensor on the at least one clamping member.

21. The method of claim 20, wherein the uterine artery is located by the blood flow sensor.

22. The method of claim 20, wherein the at least one clamping member is clamped against a portion of the vaginal wall around a portion of said uterine artery to compress the underlying uterine artery.

23. The method of claim 20, wherein the clamping member is unlocked after a predetermined time period so that said uterine artery remains occluded for only a limited time.

24. The method of claim 23, wherein said limited time ranges from about 0.5 hours and to about 4 hours.

25. A uterine artery occluding device, comprising:
   a. a first elongated pressure applying member which has a proximal handle portion, a distal handle portion and a first clamping element which is releasably disposed on the distal handle portion and which has a pressure applying surface;
   b. a second elongated pressure applying member which has a proximal handle portion, a distal handle portion and a second clamping element which is releasably disposed on the distal handle portion and which has a pressure applying surface;
   c. a pivotal connection between the first and second pressure applying members at a location proximal to the releasable clamping element and distal to the proximal handle portions thereof; and
   d. an ultrasonic blood flow sensor disposed on the pressure applying surface of at least one of the releasable clamping elements.

26. The uterine artery occluding device of claim 25 wherein the releasable clamping elements are configured to engage the patient's vaginal fornix and clamp against the tissue thereof to occlude an underlying uterine artery.

* * * * *